(12) United States Patent
Martinez Franco et al.

(10) Patent No.: US 11,560,317 B2
(45) Date of Patent: *Jan. 24, 2023

(54) METHOD FOR SYNTHESIZING AN AFX-STRUCTURE ZEOLITE OF VERY HIGH PURITY IN THE PRESENCE OF AN ORGANIC NITROGEN-CONTAINING STRUCTURING AGENT

(71) Applicant: IFP Energies nouvelles, Rueil-Malmaison (FR)

(72) Inventors: Raquel Martinez Franco, Rueil-Malmaison (FR); Bogdan Harbuzaru, Rueil-Malmaison (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 72 days.

This patent is subject to a terminal disclaimer.

(21) Appl. No.: 17/057,364

(22) PCT Filed: May 16, 2019

(86) PCT No.: PCT/EP2019/062560
§ 371 (c)(1),
(2) Date: Nov. 20, 2020

(87) PCT Pub. No.: WO2019/224088
PCT Pub. Date: Nov. 28, 2019

(65) Prior Publication Data
US 2021/0188651 A1 Jun. 24, 2021

(30) Foreign Application Priority Data
May 24, 2018 (FR) ...................... 1854389

(51) Int. Cl.
*C01B 39/48* (2006.01)
*B01J 20/18* (2006.01)
*C07D 211/14* (2006.01)

(52) U.S. Cl.
CPC ............ *C01B 39/48* (2013.01); *C07D 211/14* (2013.01); *C01P 2002/72* (2013.01); *C01P 2002/74* (2013.01); *C01P 2004/03* (2013.01)

(58) Field of Classification Search
None
See application file for complete search history.

(56) References Cited

U.S. PATENT DOCUMENTS

| | | |
|---|---|---|
| 4,508,837 A | 4/1985 | Zones |
| 5,194,235 A | 3/1993 | Zones |
| 5,958,370 A * | 9/1999 | Zones ...................... C10G 3/50 423/706 |
| 2016/0023912 A1* | 1/2016 | Goel ........................ C01B 39/38 423/709 |
| 2016/0101415 A1* | 4/2016 | Ji .......................... B01J 29/7015 423/700 |
| 2016/0137518 A1* | 5/2016 | Rivas-Cardona ........................... B01D 53/8628 423/247 |
| 2017/0304813 A1* | 10/2017 | Casci ....................... B01J 29/85 |
| 2018/0093259 A1 | 4/2018 | Chen et al. |
| 2018/0093897 A1 | 4/2018 | Chen et al. |

FOREIGN PATENT DOCUMENTS

| | | |
|---|---|---|
| JP | 2016169139 A | 9/2016 |
| WO | 2016/077667 A1 | 5/2016 |
| WO | 2017/087385 A1 | 5/2017 |
| WO | 2017/200607 A1 | 11/2017 |
| WO | 2017/202495 A1 | 11/2017 |

OTHER PUBLICATIONS

Feng, Pingyun et al. "Synthesis and Single Crystal Structure of an AFX-type . . . ". Microporous and Mesoporous Materials. 50. 145-149 (2001) (Year: 2001).*
International Search Report for PCT/EP2019/062560, dated Aug. 1, 2019; English translation submitted herewith (6 pgs.).
Martin Nuria et al. "Cage-based small-pore catalysts for NH3-SCR prepared by combining bulky organic structure directing agents with modified zeolites as reagents" Applied Catalysis B: Environmental, Elsevier, Amsterdam, NL, vol. 217, May 29, 2017 (May 29, 2017), pp. 125-136 DOI: 10.1016/J.APCATB.2017.05.082 ISSN: 0926-3373, XP085112832.

* cited by examiner

*Primary Examiner* — Sheng H Davis
(74) *Attorney, Agent, or Firm* — Fitch, Even, Tabin & Flannery, LLP

(57) ABSTRACT

The invention relates to a process for preparing an AFX-structure zeolite comprising at least the following steps:
i) mixing, in an aqueous medium, an FAU-structure zeolite having an $SiO_{2\,(FAU)}/Al_2O_{3\,(FAU)}$ molar ratio of between 6.00 and 200, limits included, an organic nitrogenous compound R, at least one source of at least one alkali and/or alkaline-earth metal M, the reaction mixture having the following molar composition: $(SiO_{2\,(FAU)})/(Al_2O_{3\,(FAU)})$ between 6.00 and 200, $H_2O/(SiO_{2\,(FAU)})$ between 1.00 and 100, $R/(SiO_{2\,(FAU)})$ between 0.01 and 0.60, $M_{2/n}O/(SiO_{2\,(FAU)})$ between 0.005 and 0.45, limits included, until a homogeneous precursor gel is obtained;
ii) hydrothermal treatment of said precursor gel obtained on conclusion of step i) at a temperature of between 120° C. and 220° C., for a time of between 12 hours and 15 days.

20 Claims, 2 Drawing Sheets

METHOD FOR SYNTHESIZING AN AFX-STRUCTURE ZEOLITE OF VERY HIGH PURITY IN THE PRESENCE OF AN ORGANIC NITROGEN-CONTAINING STRUCTURING AGENT

CROSS-REFERENCE TO RELATED APPLICATIONS

This application is a U.S. national phase application filed under 35 U.S.C. § 371 of International Application No. PCT/EP2019/062560, filed May 16, 2019, designating the United States, which claims priority from French Patent Application No. 18/54.389, filed May 24, 2018, which are hereby incorporated herein by reference in their entirety.

TECHNICAL FIELD

The present invention relates to a novel process for preparing an AFX-structure zeolite. This novel process can be used to synthesize an AFX-structure zeolite by converting/transforming an FAU-structure zeolite under hydrothermal conditions. In particular, said novel process can be used to synthesize an AFX-structure zeolite starting from an FAU-structure zeolite used as a source of silicon and aluminum and a specific organic molecule or structuring agent comprising two quaternary ammonium functions, chosen from the dihydroxide form of 1,5-bis(methylpiperidinium)pentane, 1,6-bis(methylpiperidinium)hexane or 1,7-bis(methylpiperidinium)heptane. Said AFX-structure zeolite obtained according to the process of the invention advantageously finds its application as a catalyst, adsorbent or separating agent.

PRIOR ART

Crystalline microporous materials, such as zeolites or silicoaluminophosphates, are solids that are extensively used in the petroleum industry as catalysts, catalytic supports, adsorbents or separating agents. Although many microporous crystalline structures have been discovered, the refining and petrochemical industry is constantly in search of novel zeolitic structures which have particular properties for applications such as the purification or separation of gases, the conversion of carbon-based species or the like.

AFX-structure zeolites include in particular the zeolite SSZ-16 and the zeotypes SAPO-56 and MEAPSO-56. AFX-structure zeolites have a three-dimensional system of pores delimited by eight tetrahedrons and are formed by two types of cages: gmelinite (GME cage) and a large AFT cage (~8.3×13.0 Å). Numerous methods for synthesizing AFX-structure zeolites, and in particular the zeolite SSZ-16, are known. The zeolite SSZ-16 has been synthesized using organic nitrogenous species derived from 1,4-di(1-azoniabicyclo[2.2.2]octane) lower alkane compounds (U.S. Pat. No. 4,508,837). Chevron Research and Technology Company prepared the zeolite SSZ-16 in the presence of DABCO-Cn-diquat cations, where DABCO represents 1,4-diazabicyclo[2.2.2]octane and n is 3, 4 or 5 (U.S. Pat. No. 5,194,235). S. B. Hong et al. used the diquaternary alkylammonium ion Et6-diquat-n, where Et6-diquat represents N',N'-bis-triethylpentanediammonium and n is 5, as structuring agents for synthesizing the zeolite SSZ-16 (Micropor. Mesopor. Mat., 60 (2003) 237-249). The use of 1,3-bis(adamantyl)imidazolium cations as a structuring agent for preparing AFX-structure zeolites can also be cited (R. H. Archer et al. in Micropor. Mesopor. Mat., 130 (2010) 255-2265; Johnson Matthey Company WO2016077667A1). Inagaki Satoshi et al. (JP2016169139A) used divalent N,N,N',N'-tetraarquirubicyclo[2.2.2]oct-7-ene-2,3:05,6-dipyrrolidium cations substituted with alkyl groups to prepare the zeolite SSZ-16. Chevron U.S.A. (WO2017/200607 A1) proposes the synthesis of an SSZ-16 zeolite using the dications 1,1'-(1,4-cyclohexylenedimethylene)bis[1-methylpiperidinium], 1,1'-(1,4-cyclohexylenedimethylene)bis[1-methylpyrrolidinium], 1,1'-(1,4-cyclohexylenedimethylene)bis[1-ethylpyrrolidinium]. H.-Y. Chen et al. (Johnson Matthey Company, US2018/0093897) used a mixture of cations containing at least 1,3-bis(adamantyl)imidazolium and a neutral amine to prepare the AFX-structure zeolite JMZ-10 in the absence of alkali cations. H.-Y. Chen et al. (Johnson Matthey Company, US2018/0093259) used a mixture of cations containing an organic molecule chosen from 1,3-bis(adamantyl)imidazolium, N,N-dimethyl-3,5-dimethylpiperidinium, N,N-diethyl-cis 2,6-dimethylpiperidinium, N,N,N-1-trimethyladamantylammonium, N,N,N-dimethylethylcyclohexylammonium and at least one alkaline-earth metal cation to obtain the AFX-structure zeolite JMZ-7, which has close Al sites as compared with a zeolite obtained by a synthesis using alkali cations.

DESCRIPTION OF THE INVENTION

Summary of the Invention

The invention relates to a process for preparing an AFX-structure zeolite comprising at least the following steps:
i) mixing, in an aqueous medium, an FAU-structure zeolite having an $SiO_2$ $(FAU)/Al_2O_3$ $_{(FAU)}$ molar ratio of between 6.00 and 200, limits included, an organic nitrogenous compound R, R being chosen from 1,5-bis(methylpiperidinium)pentane dihydroxide, 1,6-bis(methylpiperidinium)hexane dihydroxide or 1,7-bis(methylpiperidinium)heptane dihydroxide, at least one source of at least one alkali and/or alkaline-earth metal M of valency n, n being an integer greater than or equal to 1, M being chosen from lithium, potassium, sodium, magnesium and calcium and a mixture of at least two of these metals,
the reaction mixture having the following molar composition:
($SiO_2$ (FAU))/($Al_2O_3$ (FAU)) between 6.00 and 200, preferably between 6.00 and 100
$H_2O$/($SiO_2$ (FAU)) between 1.00 and 100, preferably between 5 and 60
R/($SiO_2$ (FAU)) between 0.01 and 0.60, preferably between 0.05 and 0.50
$M_{2/n}O$/($SiO_2$ (FAU)) between 0.005 and 0.45, preferably between 0.05 and 0.25, limits included,
in which $SiO_2$ (FAU) denotes the amount of $SiO_2$ provided by the FAU zeolite and $Al_2O_3$ $_{(FAU)}$ denotes the amount of $Al_2O_3$ provided by the FAU zeolite, until a homogeneous precursor gel is obtained;
ii) hydrothermal treatment of said precursor gel obtained on conclusion of step i) at a temperature of between 120° C. and 220° C., for a time of between 12 hours and 15 days.

R is preferably 1,6-bis(methylpiperidinium)hexane dihydroxide.

The $SiO_2/Al_2O_3$ molar ratio of the AFX zeolite obtained is advantageously between 4.00 and 100, preferably between 6.00 and 80, limits included.

Preferably, M is sodium.

The source of at least one alkali and/or alkaline-earth metal M is preferably sodium hydroxide.

In one embodiment, the reaction mixture of step i) may include at least one additional source of an $XO_2$ oxide, X being one or more tetravalent element(s) chosen from the group formed by the following elements: silicon, germanium, titanium, such that the XO2/SiO2 (FAU) molar ratio is between 0.001 and 1, preferably between 0.001 and 0.9 and more preferably between 0.001 and 0.01, limits included, the SiO2 (FAU) content in said ratio being the content provided by the FAU-structure zeolite.

In this case, the reaction mixture of step i) may have the following molar composition:
- (XO2+SiO2 (FAU))/Al2O3 (FAU) between 6.00 and 200, preferably between 6.00 and 100
- H2O/(XO2+SiO2 (FAU)) between 1 and 100, preferably between 5 and 60
- R/(XO2+SiO2 (FAU)) between 0.01 and 0.6, preferably between 0.05 and 0.5
- M2/nO/(XO2+SiO2 (FAU)) between 0.005 and 0.45, preferably between 0.05 and 0.25, limits included.

Preferably, X is silicon.

In another embodiment, the reaction mixture of step i) may include at least one additional source of a $Y_2O_3$ oxide, Y being one or more trivalent element(s) chosen from the group formed by the following elements: aluminum, boron, gallium, such that the Y2O3/Al2O3 (FAU) molar ratio is between 0.001 and 10, and preferably between 0.001 and 8, limits included, the $Al_2O_3$ $_{(FAU)}$ content in said ratio being the content provided by the FAU-structure zeolite.

In this case, the reaction mixture of step i) preferably has the following molar composition:
- SiO2 (FAU)/(Al2O3 (FAU)+Y2O3) between 6.00 and 200, preferably between 6.00 and 100
- H2O/SiO2 (FAU) between 1 and 100, preferably between 5 and 60
- R/SiO2 (FAU) between 0.01 and 0.6, preferably between 0.05 and 0.5
- M2/nO/SiO2 (FAU) between 0.005 and 0.45, preferably between 0.05 and 0.25, limits included,
- SiO2 (FAU) being the amount of SiO2 provided by the FAU zeolite and Al2O3 (FAU) being the amount of $Al_2O_3$ provided by the FAU zeolite.

Preferably, Y is aluminum.

In another embodiment, the reaction mixture of step i) may contain:
- at least one additional source of an XO2 oxide
- and at least one additional source of a Y2O3 oxide, the FAU zeolite representing between 5 and 95% by mass, preferably between 50 and 95% by mass, very preferably between 60 and 90% by mass and even more preferably between 65 and 85% by mass, relative to the total amount of trivalent and tetravalent elements SiO2 (FAU), XO2, Al2O3 (FAU) and Y2O3 in the reaction mixture, and the reaction mixture having the following molar composition:
- (XO2+SiO2 (FAU))/(Al2O3 (FAU)+Y2O3) between 6.00 and 200, preferably between 6.00 and 100
- H2O/(XO2+SiO2 (FAU)) between 1 and 100, preferably between 5 and 60
- R/(XO2+SiO2 (FAU)) between 0.01 and 0.6, preferably between 0.05 and 0.5
- M2/nO/(XO2+SiO2 (FAU)) between 0.005 and 0.45, preferably between 0.05 and 0.25, limits included.

Preferably, the precursor gel obtained on conclusion of step i) has a molar ratio of the total amount expressed as oxides of tetravalent elements to the total amount expressed as oxides of trivalent elements of between 6.00 and 100, limits included.

Advantageously, the FAU-structure zeolite has an SiO2/Al2O3 molar ratio of between 6.00 and 100, limits included.

Seed crystals of an AFX-structure zeolite may be added to the reaction mixture of step i), preferably in an amount of between 0.01 and 10% by weight relative to the total mass of the sources of the tetravalent and trivalent elements in anhydrous form present in said mixture, said seed crystals not being taken into account in the total mass of the sources of the tetravalent and trivalent elements.

Step i) may include a step of maturing the reaction mixture at a temperature of between 20 and 100° C., with or without stirring, for a time of between 30 minutes and 48 hours.

The hydrothermal treatment of step ii) may be performed under autogenous pressure at a temperature of between 120° C. and 220° C., preferably between 150° C. and 195° C., for a time of between 12 hours and 12 days, preferably between 12 hours and 8 days.

The solid phase obtained on conclusion of step ii) may be filtered off, washed, and dried at a temperature of between 20 and 150° C., preferably between 60 and 100° C., for a time of between 5 and 24 hours, to obtain a dried zeolite.

The dried zeolite may then be calcined at a temperature of between 450 and 700° C. for a time of between 2 and 20 hours, the calcination possibly being preceded by a gradual temperature increase.

The invention also relates to an AFX-structure zeolite having an SiO2/Al2O3 ratio of between 4.00 and 100, limits included, which is capable of being obtained by the preparation process described above.

The invention also relates to an AFX-structure zeolite having an SiO2/Al2O3 ratio of between 4.00 and 100, limits included, which is capable of being obtained by the preparation process described above and is calcined, and for which the mean dhkl values and relative intensities measured on an X-ray diffraction diagram are as follows:

| 2 theta (°) | dhkl (Å) | Irel | 2 theta (°) | dhkl (Å) | Irel |
|---|---|---|---|---|---|
| 7.51 | 11.77 | w | 26.09 | 3.41 | mw |
| 8.75 | 10.10 | m | 27.19 | 3.28 | vw |
| 11.72 | 7.54 | VS | 27.56 | 3.23 | vw |
| 12.98 | 6.81 | m | 28.23 | 3.15 | m |
| 14.99 | 5.90 | vw | 28.68 | 3.11 | vw |
| 15.65 | 5.66 | w | 30.23 | 2.95 | mw |
| 17.51 | 5.06 | w | 30.56 | 2.92 | m |
| 18.04 | 4.91 | m | 31.17 | 2.87 | vw |
| 19.56 | 4.53 | vw | 31.58 | 2.83 | mw |
| 19.86 | 4.47 | w | 31.91 | 2.80 | vw |
| 20.38 | 4.35 | s | 32.73 | 2.73 | vw |
| 21.84 | 4.07 | VS | 33.86 | 2.65 | mw |
| 22.28 | 3.99 | vw | 34.25 | 2.62 | vw |
| 22.55 | 3.94 | vw | 34.74 | 2.58 | w |
| 23.83 | 3.73 | w | 35.33 | 2.54 | vw | where VS=very strong; S=strong; m=moderate; mw=moderately weak; w=weak; vw=very weak. The relative intensity Irel is given in relation to a relative intensity scale in which a value of 100 is attributed to the most intense line in the X-ray diffraction diagram: vw<15; 15≤w<30; 30≤mw<50; 50≤m<65; 65≤S<85; VS≥85.

LIST OF FIGURES

Figure 1:
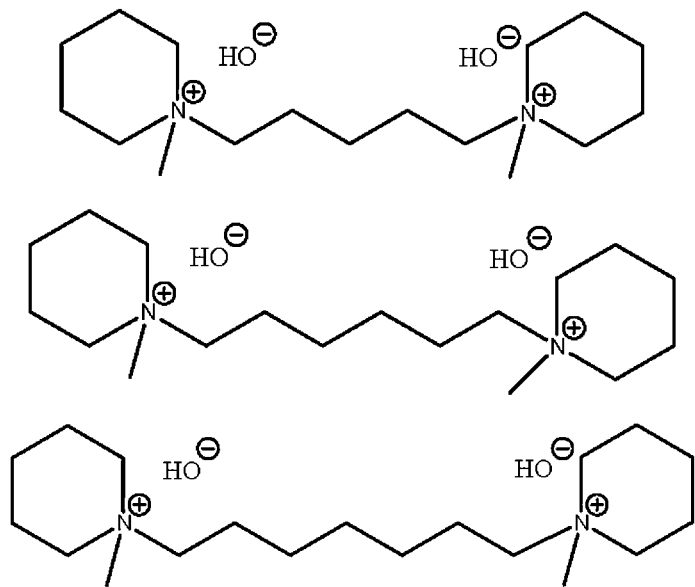
FIG. 1 represents the chemical formulae of the organic nitrogenous compounds which may be chosen as the structuring agent used in the synthesis process according to the invention.

Other characteristics and advantages of the synthesis process according to the invention will become apparent on reading the following description of non-limiting exemplary embodiments with reference to the appended figures described below.

DETAILED DESCRIPTION OF THE INVENTION

One subject of the present invention is a novel process for preparing an AFX-structure zeolite, by converting/transforming an FAU-structure zeolite under hydrothermal conditions in the presence of an organic nitrogenous compound or specific structuring agent chosen from the dihydroxide form of the following compounds:

1,5-bis(methylpiperidinium)pentane, 1,6-bis(methylpiperidinium)hexane or
1,7-bis(methylpiperidinium)heptane.

In particular, the applicant has discovered that the organic nitrogenous compound or structuring agent chosen from the dihydroxide form of 1,5-bis(methylpiperidinium)pentane, 1,6-bis (methylpiperidinium)hexane or 1,7-bis(methylpiperidinium)heptane, mixed with an FAU-structure zeolite having an SiO2 (FAU)/Al2O3 (FAU) molar ratio greater than or equal to 6.00 and less than or equal to 200, used as a source of silicon and aluminum, in the presence or absence of an additional supply, within said mixture, of at least one source of at least one tetravalent XO2 element, and/or of at least one source of at least one trivalent Y2O3 element, leads to the production of a precursor gel of an AFX-structure zeolite having a molar ratio of the total amount expressed as oxides of tetravalent elements to the total amount expressed as oxides of trivalent elements of between 6.00 and 200, then to the production of a AFX-structure zeolite of very high purity, the total amount of tetravalent element representing the sum of the SiO2 content originating from the FAU zeolite and the XO2 content originating from the possible additional source of an XO2 oxide in the case where at least one additional source of an XO2 oxide is added, the total amount of trivalent element representing the sum of the Al2O3 content originating from the FAU zeolite and the Y2O3 content originating from the possible additional source of a Y2O3 oxide in the case where at least one additional source of a Y2O3 oxide is added. Any other crystalline or amorphous phase is generally and very preferentially absent from the crystalline solid consisting of the AFX-structure zeolite obtained on conclusion of the preparation process. Advantageously, the AFX zeolite obtained has an SiO2/Al2O3 ratio of between 4.00 and 100, preferably between 6.00 and 80, limits included.

More precisely, one subject of the present invention is a novel process for preparing an AFX-structure zeolite comprising at least the following steps:

i) mixing, in an aqueous medium, an FAU-structure zeolite having an SiO2 (FAU)/Al2O3 (FAU) molar ratio of between 6 and 200, limits included, an organic nitrogenous compound R, also referred to as a specific structuring agent, chosen from 1,5-bis(methylpiperidinium)pentane dihydroxide,
1,6-bis(methylpiperidinium)hexane dihydroxide, or
1,7-bis(methylpiperidinium)heptane dihydroxide, at least one alkali metal and/or alkaline-earth metal M of valency n, n being an integer greater than or equal to 1, the mixture having the following molar composition:

(SiO2 (FAU))/(Al2O3 (FAU)) between 6.00 and 200, preferably between 6.00 and 100
H2O/(SiO2 (FAU)) between 1 and 100, preferably between 5 and 60
R/(SiO2 (FAU)) between 0.01 and 0.6, preferably between 0.05 and 0.5
M2/nO/(SiO2 (FAU)) between 0.005 and 0.45, preferably between 0.05 and 0.25 in which SiO2 (FAU) is the amount of SiO2 provided by the FAU zeolite and Al2O3 (FAU) is the amount of Al2O3 provided by the FAU zeolite, H2O is the molar amount of water present in the reaction mixture, R is the molar amount of said organic nitrogenous compound, M2/nO is the molar amount expressed in the form of M2/nO oxide of the source of alkali metal and/or of alkaline-earth metal, and M is one or more alkali and/or alkaline-earth metal(s) chosen from lithium, sodium, potassium, calcium, magnesium and a mixture of at least two of these metals, very preferably M is sodium, step i) being performed for a time enabling a homogeneous mixture known as a precursor gel to be obtained;

ii) hydrothermal treatment of said precursor gel obtained on conclusion of step i), at a temperature of between 120° C. and 220° C. for a time of between 12 hours and 15 days, until said AFX-structure zeolite forms.

One advantage of the present invention is thus that it provides a novel preparation process for forming an AFX-structure zeolite of very high purity starting from an FAU-structure zeolite, said process being performed in the presence of a specific organic structuring agent chosen from 1,5-bis(methylpiperidinium)pentane dihydroxide,
1,6-bis(methylpiperidinium)hexane dihydroxide or
1,7-bis(methylpiperidinium)heptane dihydroxide.

Another advantage of the present invention is that it allows for the preparation of a precursor gel of an AFX-structure zeolite having an SiO2/Al2O3 molar ratio that is identical to, greater than or less than the SiO2 (FAU)/Al2O3 (FAU) molar ratio of the starting FAU-structure zeolite.

The starting FAU-structure zeolite having an SiO2/Al2O3 molar ratio of between 6 and 200, limits included, may be obtained by any method known to a person skilled in the art, for example by steaming and acid washes on an FAU-structure zeolite having an SiO2/Al2O3 molar ratio of less than 6.00. As FAU sources having an SiO2/Al2O3 ratio greater than or equal to 6.00, mention may be made of the commercial zeolites CBV712, CBV720, CBV760 and CBV780 produced by Zeolyst and the commercial zeolites HSZ-350HUA, HSZ-360HUA and HSZ-385HUA produced by TOSOH.

The preparation process according to the invention thus allows the SiO2/Al2O3 ratio of the precursor gel containing an FAU-structure zeolite to be adjusted as a function of the chosen FAU-structure zeolite and of the additional supply or not, within the reaction mixture, of at least one source of at least one tetravalent XO2 element and/or of at least one source of at least one trivalent Y2O3 element.

Step i) comprises mixing, in an aqueous medium, an FAU-structure zeolite having an SiO2 (FAU)/Al2O3 (FAU) molar ratio of between 6 and 200, limits included, an organic nitrogenous compound R, R being 1,5-bis(methylpiperidinium)pentane dihydroxide,
1,6-bis(methylpiperidinium)hexane dihydroxide, or
1,7-bis(methylpiperidinium)heptane dihydroxide, at least one alkali metal and/or alkaline-earth metal M of valency n, n being an integer greater than or equal to 1, the reaction mixture having the following molar composition:

(SiO2 (FAU))/(Al2O3 (FAU)) between 6.00 and 200, preferably between 6.00 and 100

H2O/(SiO2 (FAU)) between 1 and 100, preferably between 5 and 60

R/(SiO2 (FAU)) between 0.01 and 0.6, preferably between 0.05 and 0.5

M2/nO/(SiO2 (FAU)) between 0.005 and 0.45, preferably between 0.05 and 0.25 in which SiO2 (FAU) is the amount of SiO2 provided by the FAU zeolite and Al2O3 (FAU) is the amount of Al2O3 provided by the FAU zeolite, and M is one or more alkali and/or alkaline-earth metal(s) chosen from lithium, sodium, potassium, calcium, magnesium and a mixture of at least two of these metals, M very preferably being sodium.

In a preferred embodiment, the reaction mixture of step i) also includes at least one additional source of an XO2 oxide, such that the XO2/SiO2 (FAU) molar ratio is between 0.001 and 1, the mixture advantageously having the following molar composition:

(XO2+SiO2 (FAU))/Al2O3 (FAU) between 6.00 and 200, preferably between 6.00 and 100

H2O/(XO2+SiO2 (FAU)) between 1 and 100, preferably between 5 and 60

R/(XO2+SiO2 (FAU)) between 0.01 and 0.6, preferably between 0.05 and 0.5

M2/nO/(XO2+SiO2 (FAU)) between 0.005 and 0.45, preferably between 0.05 and 0.25 in which X is one or more tetravalent element(s) chosen from the group formed by the following elements: silicon, germanium, titanium, X preferably being silicon, SiO2 (FAU) being the amount of SiO2 provided by the FAU zeolite and Al2O3 (FAU) being the amount of Al2O3 provided by the FAU zeolite, R being 1,5-bis(methylpiperidinium)pentane dihydroxide, 1,6-bis(methylpiperidinium)hexane dihydroxide or 1,7-bis(methylpiperidinium)heptane dihydroxide, and M is one or more alkali and/or alkaline-earth metal(s) chosen from lithium, sodium, potassium, calcium, magnesium and a mixture of at least two of these metals, M very preferably being sodium.

In another preferred embodiment, the reaction mixture of step i) also includes at least one additional source of a Y2O3 oxide, such that the Y2O3/Al2O3 (FAU) molar ratio between 0.001 and 10, the mixture advantageously having the following molar composition:

SiO2 (FAU)/(Al2O3 (FAU)+Y2O3) between 6.00 and 200, preferably between 6.00 and 100

H2O/SiO2 (FAU) between 1 and 100, preferably between 5 and 60

R/SiO2 (FAU) between 0.01 and 0.6, preferably between 0.05 and 0.5

M2/nO/SiO2 (FAU) between 0.005 and 0.45, preferably between 0.05 and 0.25 in which Y is one or more trivalent element(s) chosen from the group formed by the following elements: aluminum, boron, gallium, Y preferably being aluminum, SiO2 (FAU) being the amount of SiO2 provided by the FAU zeolite and Al2O3 (FAU) being the amount of Al2O3 provided by the FAU zeolite, R being 1,5-bis(methylpiperidinium)pentane dihydroxide, 1,6-bis(methylpiperidinium)hexane dihydroxide or 1,7-bis(methylpiperidinium)heptane dihydroxide, and M is one or more alkali and/or alkaline-earth metals chosen from lithium, sodium, potassium, calcium, magnesium and a mixture of at least two of these metals, M very preferably being sodium.

In another preferred embodiment, the reaction mixture of step i) contains a percentage of between 5 and 95% by mass, preferably between 50 and 95% by mass, very preferably between 60 and 90% by mass and even more preferably between 65 and 85% by mass of an FAU-structure zeolite relative to the total amount of sources of trivalent and tetravalent elements of the mixture and also includes at least one additional source of an XO2 oxide and at least one additional source of a Y2O3 oxide, the reaction mixture having the following molar composition:

(XO2+SiO2 (FAU))/(Al2O3 (FAU)+Y2O3) between 6.00 and 200, preferably between 6.00 and 100

H2O/(XO2+SiO2 (FAU)) between 1 and 100, preferably between 5 and 60

R/(XO2+SiO2 (FAU)) between 0.01 and 0.6, preferably between 0.05 and 0.5

M2/nO/(XO2+SiO2 (FAU)) between 0.005 and 0.45, preferably between 0.05 and 0.25 in which X is one or more tetravalent element(s) chosen from the group formed by the following elements: silicon, germanium, titanium, X preferably being silicon, Y is one or more trivalent element(s) chosen from the group formed by the following elements: aluminum, boron, gallium, preferably aluminum, SiO2 (FAU) being the amount of SiO2 provided by the FAU zeolite and Al2O3 (FAU) being the amount of Al2O3 provided by the FAU zeolite, R being 1,5-bis(methylpiperidinium)pentane dihydroxide, 1,6-bis(methylpiperidinium)hexane dihydroxide or 1,7-bis(methylpiperidinium)heptane dihydroxide, and M is one or more alkali and/or alkaline-earth metals chosen from lithium, sodium, potassium, calcium, magnesium and a mixture of at least two of these metals, M very preferably being sodium.

Step i) enables a homogeneous precursor gel to be obtained.

Step ii) comprises a hydrothermal treatment of said precursor gel obtained on conclusion of step i), which is carried out at a temperature of between 120° C. and 220° C. for a time of between 12 hours and 15 days, until said AFX-structure zeolite crystallizes.

In accordance with the invention, an FAU-structure zeolite having an SiO2 (FAU)/Al2O3 (FAU) molar ratio of between 6 and 200, limits included, preferably of between 6.00 and 100, limits included, is incorporated into the reaction mixture for the performance of step (i) as a source of silicon and aluminum elements.

In accordance with the invention, R is an organic nitrogenous compound chosen from 1,5-bis(methylpiperidinium)pentane dihydroxide, 1,6-bis(methylpiperidinium)hexane dihydroxide or 1,7-bis(methylpiperidinium)heptane dihydroxide, said compound being incorporated into the reaction mixture for the performance of step (i) as an organic structuring agent. The anion associated with the quaternary ammonium cations present in the organic structuring species for the synthesis of an AFX-structure zeolite according to the invention is the hydroxide anion.

In accordance with the invention, at least one source of at least one alkali and/or alkaline-earth metal M of valency n is used in the reaction mixture of step i), n being an integer greater than or equal to 1, M preferably being chosen from lithium, potassium, sodium, magnesium and calcium and a mixture of at least two of these metals. Very preferably, M is sodium.

The source of at least one alkali and/or alkaline-earth metal M is preferably sodium hydroxide.

In accordance with the invention, at least one additional source of an $XO_2$ oxide, X being one or more tetravalent element(s) chosen from the group formed by the following elements: silicon, germanium, titanium, and X preferably being silicon, such that the $XO_2/SiO_2$ (FAU) molar ratio is between 0.001 and 1, preferably between 0.001 and 0.9 and more preferably between 0.001 and 0.01, the $SiO_2$ (FAU) content in said ratio being the content provided by the FAU-structure zeolite, is advantageously used in the reaction mixture of step i).

In particular, adding at least one additional source of an $XO_2$ oxide enables the $XO_2/Y_2O_3$ ratio of the precursor gel of an AFX-structure zeolite obtained on conclusion of step i) to be adjusted.

The source(s) of said tetravalent element(s) may be any compound comprising the element X and which can release this element in aqueous solution in reactive form. When X is titanium, $Ti(EtO)_4$ is advantageously used as the source of titanium.

In the preferred case in which X is silicon, the source of silicon may be any one of said sources commonly used for zeolite synthesis, for example powdered silica, silicic acid, colloidal silica, dissolved silica or tetraethoxysilane (TEOS). Among the powdered silicas, use may be made of precipitated silicas, especially those obtained by precipitation from a solution of alkali metal silicate, fumed silicas, for example Cab-O-Sil, and silica gels. Colloidal silicas having various particle sizes, for example a mean equivalent diameter of between 10 and 15 nm or between 40 and 50 nm, may be used, such as those sold under registered brand names such as Ludox. Preferably, the source of silicon is Cab-O-Sil.

In accordance with the invention, at least one additional source of a $Y_2O_3$ oxide, Y being one or more trivalent element(s) chosen from the group formed by the following elements: aluminum, boron, gallium, is advantageously used in the mixture of step i). Preferably, Y is aluminum, such that the $Y_2O_3/Al_2O_3$ (FAU) molar ratio is between 0.001 and 10, and preferably between 0.001 and 8, the $Al_2O_3$ (FAU) content in said ratio being the content provided by the FAU-structure zeolite.

Adding at least one additional source of a $Y_2O_3$ oxide thus enables the $XO_2/Y_2O_3$ ratio of the precursor gel of an AFX-structure zeolite obtained on conclusion of step i) to be adjusted.

The source(s) of said trivalent element(s) Y may be any compound comprising the element Y and which can release this element in aqueous solution in reactive form. Element Y may be incorporated into the mixture in an oxidized form $YO_b$ with $1 \leq b \leq 3$ (b being an integer or a rational number) or in any other form. In the preferred case where Y is aluminum, the source of aluminum is preferably aluminum hydroxide or an aluminum salt, for example chloride, nitrate or sulfate, a sodium aluminate, an aluminum alkoxide, or alumina itself, preferably in hydrated or hydratable form, for instance colloidal alumina, pseudoboehmite, gamma-alumina or alpha or beta trihydrate. Use may also be made of mixtures of the sources mentioned above.

Step (i) of the process according to the invention consists in preparing an aqueous reaction mixture containing an FAU-structure zeolite, optionally a source of an $XO_2$ oxide or a source of a $Y_2O_3$ oxide, at least one organic nitrogenous compound R, R being chosen from 1,5-bis(methylpiperidinium)pentane dihydroxide, 1,6-bis(methylpiperidinium) hexane dihydroxide or 1,7-bis(methylpiperidinium)heptane dihydroxide, in the presence of at least one source of one or more alkali and/or alkaline-earth metal(s), to obtain a precursor gel of an AFX-structure zeolite. The amounts of said reagents are adjusted in the manner described above so as to give this gel a composition allowing an AFX-structure zeolite to be crystallized.

It may be advantageous to add seeds of an AFX-structure zeolite to the reaction mixture during said step i) of the process of the invention so as to reduce the time required for the formation of the crystals of an AFX-structure zeolite and/or the total crystallization time. Said seed crystals also promote the formation of said AFX-structure zeolite to the detriment of impurities. Such seeds comprise crystalline solids, in particular crystals of an AFX-structure zeolite. The seed crystals are generally added in a proportion of between 0.01% and 10% of the total anhydrous mass of the sources of said tetravalent and trivalent element(s) used in the reaction mixture, said seed crystals not being taken into account in the total mass of the sources of the tetravalent and trivalent elements. Said seeds are not taken into account either for determining the composition of the reaction mixture and/or of the gel, defined above, i.e. in the determination of the various molar ratios of the composition of the reaction mixture.

The mixing step i) is performed until a homogeneous mixture is obtained, preferably for a time of greater than or equal to 15 minutes, preferably with stirring by any system known to those skilled in the art, at a low or high shear rate.

On conclusion of step i), a homogeneous precursor gel is obtained.

It may be advantageous to perform a maturation of the reaction mixture during said step i) of the process according to the invention, before the hydrothermal crystallization, so as to control the size of the crystals of an AFX-structure zeolite. Said maturation also promotes the formation of said AFX-structure zeolite to the detriment of impurities. Maturation of the reaction mixture during said step i) of the process of the invention may be performed at room temperature or at a temperature of between 20 and 100° C. with or without stirring, for a time advantageously of between 30 minutes and 48 hours.

In accordance with step (ii) of the process according to the invention, the precursor gel obtained on conclusion of step i) is subjected to a hydrothermal treatment, preferably performed at a temperature of between 120° C. and 220° C. for a time of between 12 hours and 15 days, until said AFX-structure zeolite forms.

The precursor gel is advantageously placed under hydrothermal conditions under an autogenous reaction pressure, optionally with addition of gas, for example nitrogen, at a temperature preferably of between 120° C. and 220° C., preferably between 150° C. and 195° C., until an AFX-structure zeolite has fully crystallized.

The time required to obtain crystallization ranges between 12 hours and 15 days, preferably between 12 hours and 12 days and more preferably between 12 hours and 8 days.

The reaction is generally performed with or without stirring, preferably with stirring. The stirring system that may be used is any system known to those skilled in the art, for example inclined paddles with counter-blades, stirring turbomixers or endless screws.

At the end of the reaction, after performing said step ii) of the preparation process according to the invention, the solid phase formed from an AFX-structure zeolite is preferably filtered off, washed and then dried. The drying is generally performed at a temperature of between 20° C. and 150° C., preferably between 60° C. and 100° C., for a time of between 5 and 24 hours.

The dried zeolite may then advantageously be calcined. The calcined AFX-structure zeolite is generally analyzed by X-ray diffraction, this technique also making it possible to determine the purity of said zeolite obtained via the process of the invention.

Very advantageously, the process of the invention leads to the formation of an AFX-structure zeolite, free of any other crystalline or amorphous phase. Said AFX-structure zeolite, after the drying step, is then ready for subsequent steps such as calcination and ion exchange. For these steps, any conventional method known to those skilled in the art may be employed.

The loss on ignition of said AFX-structure zeolite obtained after drying and before calcination is generally between 5 and 15% by weight. According to the invention, loss on ignition (LOI) refers to the percentage loss in mass experienced by a solid compound, a mixture of solid compounds or a paste, in the case of the present invention preferably by said prepared AFX zeolite, during a heat treatment at 1000° C. for 2 hours, in a static oven (of muffle furnace type), relative to the mass of the solid compound, of the mixture of solid compounds or of the paste in its initial form, in the case of the present invention preferably relative to the mass of the dried AFX zeolite that was tested. The loss on ignition corresponds in general to the loss of solvent (such as water) present in the solids, but also to the removal of organic compounds contained in the inorganic solid constituents.

The step of calcining an AFX-structure zeolite obtained according to the process of the invention is preferably performed at a temperature of between 450 and 700° C. for a time of between 2 and 20 hours.

The AFX-structure zeolite obtained on conclusion of the calcining step is free of any organic species and in particular of the organic structuring agent R.

On conclusion of said calcining step, X-ray diffraction makes it possible to confirm that the solid obtained via the process according to the invention is indeed an AFX-structure zeolite. The purity obtained is advantageously greater than 95% and preferably greater than 99.8% by weight. The solid obtained has the X-ray diffraction pattern which includes at least the lines recorded in Table 1. Preferably, the X-ray diffraction pattern does not contain any other lines of significant intensity (i.e. with an intensity greater than about three times the background noise) than those recorded in Table 1.

This diffraction pattern is obtained by radiocrystallographic analysis by means of a diffractometer using the conventional powder method with the Kα1 radiation of copper ($\lambda$=1.5406 Å). On the basis of the position of the diffraction peaks represented by the angle 2θ, the lattice constant distances dhkl characteristic of the sample are calculated using the Bragg relationship. The measurement error Δ(dhkl) on dhkl is calculated by means of the Bragg relationship as a function of the absolute error Δ(2θ) assigned to the measurement of 2θ. An absolute error Δ(2θ) equal to ±0.02° is commonly accepted. The relative intensity Irel assigned to each value of dhkl is measured according to the height of the corresponding diffraction peak. The X-ray diffraction pattern of the AFX-structure crystalline solid according to the invention includes at least the lines at the values of dhkl given in Table 1. In the column of the dhkl values, the mean values of the inter-lattice distances are given in Angstroms (Å). Each of these values must be assigned the measurement error Δ(dhkl) of between ±0.6 Å and 0.01 Å.

| 2 theta (°) | dhkl (Å) | Irel | 2 theta (°) | dhkl (Å) | Irel |
|---|---|---|---|---|---|
| 7.51 | 11.77 | w | 26.09 | 3.41 | mw |
| 8.75 | 10.10 | m | 27.19 | 3.28 | vw |
| 11.72 | 7.54 | VS | 27.56 | 3.23 | vw |
| 12.98 | 6.81 | m | 28.23 | 3.15 | m |
| 14.99 | 5.90 | vw | 28.68 | 3.11 | vw |
| 15.65 | 5.66 | w | 30.23 | 2.95 | mw |
| 17.51 | 5.06 | w | 30.56 | 2.92 | m |
| 18.04 | 4.91 | m | 31.17 | 2.87 | vw |
| 19.56 | 4.53 | vw | 31.58 | 2.83 | mw |
| 19.86 | 4.47 | w | 31.91 | 2.80 | vw |
| 20.38 | 4.35 | s | 32.73 | 2.73 | vw |
| 21.84 | 4.07 | VS | 33.86 | 2.65 | mw |
| 22.28 | 3.99 | vw | 34.25 | 2.62 | vw |
| 22.55 | 3.94 | vw | 34.74 | 2.58 | w |
| 23.83 | 3.73 | w | 35.33 | 2.54 | vw | where VS=very strong; S=strong; m=medium; mw=moderately weak; w=weak; vw=very weak. The relative intensity Irel is given as a relative intensity scale in which a value of 100 is attributed to the most intense line in the x-ray diffraction diagram: vw<15; 15≤w<30; 30≤mw<50; 50≤m<65; 65≤S<85; VS≥85.

X-ray fluorescence spectrometry (XFS) is a chemical analysis technique using a physical property of matter, X-ray fluorescence. It enables the analysis of the majority of the chemical elements starting from beryllium (Be) in concentration ranges ranging from a few ppm to 100%, with precise and reproducible results. X-rays are used to excite the atoms in a sample, which makes them emit X-rays having an energy characteristic of each element present. The intensity and the energy of these X-rays are then measured to determine the concentration of the elements in the material.

It is also advantageous to obtain the protonated form of the AFX-structure zeolite obtained via the process according to the invention. Said hydrogen form may be obtained by performing an ion exchange with an acid, in particular a strong mineral acid such as hydrochloric, sulfuric or nitric acid, or with a compound such as ammonium chloride, sulfate or nitrate. The ion exchange may be performed by placing said AFX-structure zeolite in suspension one or more times with the ion-exchange solution. Said zeolite may be calcined before or after the ion exchange or between two ion-exchange steps. The zeolite is preferably calcined before the ion exchange, so as to remove any organic substance included in the porosity of the zeolite, since the ion exchange is thereby facilitated.

The AFX-structure zeolite obtained via the process of the invention may be used after ion exchange as acidic solid for catalysis in the fields of refining and petrochemistry. It may also be used as an absorbent or as a molecular sieve.

EXAMPLES

The invention is illustrated by the examples that follow, which are not in any way limiting in nature.

Example 1: Preparation of 1,6-bis(methylpiperidinium)hexane dihydroxide (Structuring Agent R)

50 g of 1,6-dibromohexane (0.20 mol, 99%, Alfa Aesar) are placed in a 1 L round-bottomed flask containing 50 g of N-methylpiperidine (0.51 mol, 99%, Alfa Aesar) and 200 mL of ethanol. The reaction medium is stirred at reflux for 5 hours. The mixture is then cooled to room temperature and then filtered. The mixture is poured into 300 mL of cold diethyl ether and the precipitate formed is then filtered off and washed with 100 mL of diethyl ether. The solid obtained is recrystallized from an ethanol/ether mixture. The solid obtained is dried under vacuum for 12 hours. 71 g of a white solid are obtained (i.e. a yield of 80%).

The product has the expected 1H NMR spectrum. 1H NMR (D2O, ppm/TMS): 1.27 (4H, m); 1.48 (4H, m); 1.61 (4H, m); 1.70 (8H, m); 2.85 (6H, 5), 3.16 (12H, m).

18.9 g of Ag2O (0.08 mol, 99%, Aldrich) are placed in a 250 mL Teflon beaker containing 30 g of the prepared structuring agent 1,6-bis(methylpiperidinium)hexane dibromide (0.07 mol) and 100 mL of deionized water. The reaction medium is stirred for 12 hours in the absence of light. The mixture is then filtered. The filtrate obtained is composed of an aqueous solution of 1,6-bis(methylpiperidinium)hexane dihydroxide. Assay of this species is performed by proton NMR using formic acid as standard.

Example 2: Preparation of an AFX-Structure Zeolite According to the Invention 392 mg of an FAU-structure zeolite (CBV720, SiO2/Al2O3=33.52, Zeolyst, LOI=6.63%) were mixed with 1.436 g of an aqueous solution of 1,6-bis(methylpiperidinium)hexane dihydroxide (21.56% by weight) prepared in accordance with Example 1. 2.054 g of deionized water are added to the previous mixture, and the preparation obtained is kept stirring for 10 minutes. In order to promote the formation of an AFX-structure zeolite, 37 mg of seeds (9.4% relative to the mass of the zeolite CBV720) of an AFX-structure zeolite prepared in accordance with Example 10 are added to the synthesis mixture and kept stirring for 5 minutes. 368 mg of an aqueous solution containing 20% by weight of sodium hydroxide (98% by weight, Aldrich) were incorporated into the synthesis mixture, which is kept stirring for half an hour. The molar composition of the precursor gel is as follows: 1 SiO2:0.03 Al2O3:0.17 R:0.16 Na2O:34 H2O, i.e. an SiO2/Al2O3 ratio of 33.3. The precursor gel is then transferred, after homogenization, into an autoclave. The autoclave is closed and then heated for 22 hours at 180° C. with stirring at 35 rpm with a rotary spit system. The solid obtained is filtered off, washed with deionized water and then dried overnight at 100° C. The loss on ignition of the dried solid is 10%. The solid is then introduced into a muffle furnace where a calcination step is performed: the calcination cycle comprises an increase in temperature of 1.5° C./minute up to 200° C., a steady stage at 200° C. maintained for 2 hours, an increase in temperature of 1° C./minute up to 550° C., followed by a steady stage at 550° C. maintained for 8 hours, then return to room temperature.

The calcined solid product was analyzed by X-ray diffraction and identified as consisting of an AFX-structure zeolite with a purity of greater than 99% by weight.

Example 3: Preparation of an AFX-Structure Zeolite According to the Invention 3.219 g of an FAU-structure zeolite (CBV720, SiO2/Al2O3=33.52, Zeolyst, LOI=6.63%) were mixed with 11.796 g of an aqueous solution of 1,6-bis(methylpiperidinium)hexane dihydroxide (21.56% by weight) prepared in accordance with Example 1. 17.583 g of deionized water are added to the previous mixture, and the preparation obtained is kept stirring for 10 minutes. In order to promote the formation of an AFX-structure zeolite, 302 mg of seeds (9.4% relative to the mass of zeolite CBV720) of an AFX-structure zeolite prepared in accordance with Example 10 are added to the synthesis mixture and kept stirring for 5 minutes. 3.214 g of an aqueous solution containing 20% by weight of sodium hydroxide (98% by weight, Aldrich) were incorporated into the synthesis mixture, which is kept stirring for half an hour. The molar composition of the precursor gel is as follows: 1 SiO2:0.03 Al2O3:0.17 R:0.17 Na2O:35 H2O, i.e. an SiO2/Al2O3 ratio of 33.3. The precursor gel is then transferred, after homogenization, into a 160 mL stainless-steel reactor equipped with a stirring system with four inclined paddles. The reactor is closed and then heated for 22 hours at 180° C. with stirring at 250 rpm. The crystalline product obtained is filtered off, washed with deionized water and then dried overnight at 100° C. The loss on ignition of the dried solid is 9.5%. The solid is then introduced into a muffle furnace where a calcination step is performed: the calcination cycle comprises an increase in temperature of 1.5° C./minute up to 200° C., a steady stage at 200° C. maintained for 2 hours, an increase in temperature of 1° C./minute up to 550° C., followed by a steady stage at 550° C. maintained for 8 hours, then return to room temperature.

The calcined solid product was analyzed by X-ray diffraction and identified as consisting of an AFX-structure zeolite with a purity of greater than 99% by weight.

Example 4: Preparation of an AFX-Structure Zeolite According to the Invention 601 mg of an FAU-structure zeolite (CBV720, SiO2/Al2O3=33.52, Zeolyst, LOI=6.63%) were mixed with 2.204 g of an aqueous solution of 1,6-bis(methylpiperidinium)hexane dihydroxide (21.56% by weight) prepared in accordance with Example 1. 3.164 g of deionized water are added to the previous mixture, and the preparation obtained is kept stirring for 10 minutes. 600 mg of an aqueous solution containing 20% by weight of sodium hydroxide (98% by weight, Aldrich) were incorporated into the synthesis mixture, which is kept stirring for half an hour. The molar composition of the precursor gel is as follows: 1 SiO2:0.03 Al2O3:0.17 R:0.17 Na2O:34 H2O, i.e. an SiO2/Al2O3 ratio of 33.33. The precursor gel is then transferred, after homogenization, into an autoclave. The autoclave is closed and then heated for 24 hours at 180° C. with stirring at 35 rpm with a rotary spit system. The crystalline product obtained is filtered off, washed with deionized water and then dried overnight at 100° C. The loss on ignition of the dried solid is 10%. The solid is then introduced into a muffle furnace where a calcination step is performed: the calcination cycle comprises an increase in temperature of 1.5° C./minute up to 200° C., a steady stage at 200° C. maintained for 2 hours, an increase in temperature of 1° C./minute up to 550° C., followed by a steady stage at 550° C. maintained for 8 hours, then return to room temperature.

The calcined solid product was analyzed by X-ray diffraction and identified as consisting of an AFX-structure zeolite with a purity of greater than 99% by weight. The product has an SiO2/Al2O3 molar ratio of 15.5 as determined by X-ray fluorescence.

Example 5: Preparation of an AFX-Structure Zeolite According to the Invention 240 mg of an FAU-structure zeolite (CBV720, SiO2/Al2O3=33.52, Zeolyst, LOI=6.63%) were mixed with 1.048 g of an aqueous solution of 1,6-bis(methylpiperidinium) hexane dihydroxide (21.56% by weight) prepared in accordance with Example 1. 1.655 g of deionized water are added to the previous mixture, and the preparation obtained is kept stirring for 10 minutes. In order to promote the formation of an AFX-structure zeolite, 24 mg of seeds (10% relative to the mass of zeolite CBV720) of an AFX-structure zeolite prepared in accordance with Example 10 are added to the synthesis mixture and kept stirring for 5 minutes. 269 mg of an aqueous solution containing 20% by weight of sodium hydroxide (98% by weight, Aldrich) are added to the synthesis mixture and kept stirring for 15 minutes. 41 mg of Cab-O-Sil M5 fumed silica (100% by weight of $SiO_2$, Cabot), corresponding to an ($SiO_2$(Cab-O-Sil)/$SiO_2$(FAU)) molar ratio of 0.002 (and to a mass amount of seeds of 8.5% relative to the total mass of the zeolite CBV720 and the added Cab-O-Sil silica), were then incorporated into the synthesis mixture, which is kept stirring for half an hour. The molar composition of the precursor gel is as follows: 1 $SiO_2$:0.025 $Al_2O_3$:0.17 R:0.16 $Na_2O$:36 $H_2O$, i.e. an $SiO_2$/$Al_2O_3$ ratio of 40. The precursor gel is then transferred, after homogenization, into an autoclave. The autoclave is closed and then heated for 4 days at 180° C. with stirring at 35 rpm with a rotary spit system. The crystalline product obtained is filtered off, washed with deionized water and dried overnight at 100° C. The loss on ignition of the dried solid is 9.5%. The solid is then introduced into a muffle furnace where a calcination step is performed: the calcination cycle comprises an increase in temperature of 1.5° C./minute up to 200° C., a steady stage at 200° C. maintained for 2 hours, an increase in temperature of 1° C./minute up to 550° C., followed by a steady stage at 550° C. maintained for 8 hours, then return to room temperature.

The calcined solid product was analyzed by X-ray diffraction and identified as consisting of an AFX-structure zeolite with a purity of greater than 99%.

Example 6: Preparation of an AFX-Structure Zeolite According to the Invention 5.712 g of an FAU-structure zeolite (CBV720, $SiO_2$/$Al_2O_3$=33.52, Zeolyst, LOI=6.63) were mixed with 26.416 g of an aqueous solution of 1,6-bis(methylpiperidinium) hexane dihydroxide (21.56% by weight) prepared in accordance with Example 1. 37.62 g of deionized water are added to the previous mixture, and the preparation obtained is kept stirring for 10 minutes. In order to promote the formation of an AFX-structure zeolite, 571 mg of seeds (10% relative to the mass of zeolite CBV720) of an AFX-structure zeolite prepared in accordance with Example 10 are added to the synthesis mixture and kept stirring for 5 minutes. 7.117 g of an aqueous solution containing 20% by weight of sodium hydroxide (98% by weight, Aldrich) are added to the synthesis mixture and kept stirring for 15 minutes. 0.965 g of Cab-O-Sil M5 fumed silica (100% by weight of $SiO_2$, Cabot), corresponding to an ($SiO_2$(Cab-O-Sil)/$SiO_2$(FAU)) molar ratio of 0.002 (and to a mass amount of seeds of 8.55% relative to the total mass of the zeolite CBV720 and the added Cab-O-Sil silica), were then incorporated into the synthesis mixture, which is kept stirring for half an hour. The molar composition of the precursor gel is as follows: 1 $SiO_2$:0.025 $Al_2O_3$:0.18 R:0.178 $Na_2O$:36 $H_2O$, i.e. an $SiO_2$/$Al_2O_3$ ratio of 40.

The precursor gel is then transferred, after homogenization, into a 160 mL stainless-steel reactor equipped with a stirring system with four inclined paddles. The reactor is closed and then heated for 30 hours at 180° C. with stirring at 250-300 rpm. The crystalline product obtained is filtered off, washed with deionized water and dried overnight at 100° C. The loss on ignition of the dried solid is 9.6%. The solid is then introduced into a muffle furnace where a calcination step is performed: the calcination cycle comprises an increase in temperature of 1.5° C./minute up to 200° C., a steady stage at 200° C. maintained for 2 hours, an increase in temperature of 1° C./minute up to 550° C., followed by a steady stage at 550° C. maintained for 8 hours, then return to room temperature.

The calcined solid product was analyzed by X-ray diffraction and identified as consisting of an AFX-structure zeolite with a purity of greater than 99% by weight. The product has an $SiO_2$/$Al_2O_3$ molar ratio of 12.85 as determined by X-ray fluorescence.

Example 7: Preparation of an AFX-Structure Zeolite According to the Invention 361 mg of an FAU-structure zeolite (CBV712, $SiO_2$/$Al_2O_3$=11.47, Zeolyst, LOI=12.81%) were mixed with 2.357 g of an aqueous solution of 1,6-bis(methylpiperidinium)hexane dihydroxide (20.9% by weight) prepared in accordance with Example 1. The mixture obtained is kept stirring for 10 minutes. 258 mg of an aqueous solution containing 20% by weight of sodium hydroxide (98% by weight, Aldrich) and 245 mg of deionized water are added to the synthesis mixture and kept stirring for 10 minutes. 199 mg of Cab-O-Sil M5 fumed silica (100% by weight of $SiO_2$, Cabot), corresponding to an ($SiO_2$(Cab-O-Sil)/$SiO_2$(FAU)) molar ratio of 0.007, were then incorporated into the synthesis mixture, which is kept stirring for one hour. The precursor gel obtained has the following molar composition: 1 $SiO_2$:0.05 $Al_2O_3$:0.20 R:0.083 $Na_2O$:17 $H_2O$, i.e. an $SiO_2$/$Al_2O_3$ ratio of 20. The mixture is then transferred, after homogenization, into an autoclave. The autoclave is closed and then heated for 6 days at 170° C. with stirring at 35 rpm with a rotary spit system. The crystalline product obtained is filtered off, washed with deionized water and then dried overnight at 100° C. The loss on ignition of the dried solid is 9.5%. The solid is then introduced into a muffle furnace where a calcination step is performed: the calcination cycle comprises an increase in temperature of 1.5° C./minute up to 200° C., a steady stage at 200° C. maintained for 2 hours, an increase in temperature of 1° C./minute up to 550° C., followed by a steady stage at 550° C. maintained for 8 hours, then return to room temperature.

Figure 2:
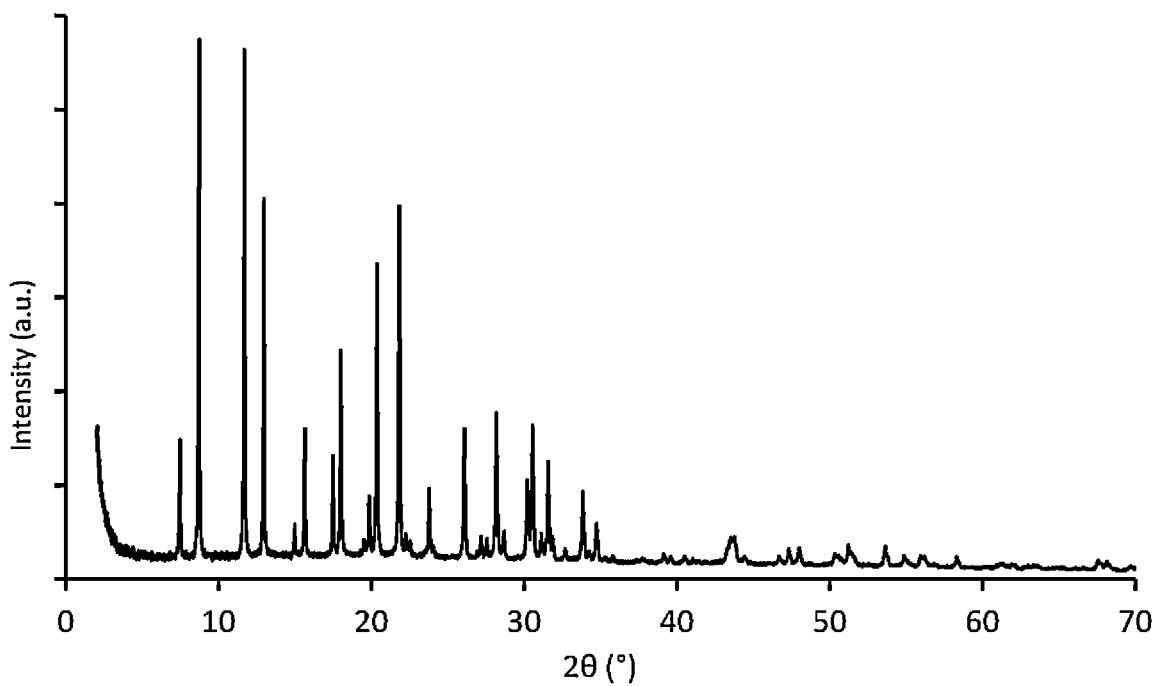
FIG. 2 represents the X-ray diffraction pattern of the AFX zeolite obtained according to Example 7.
Figure 3:
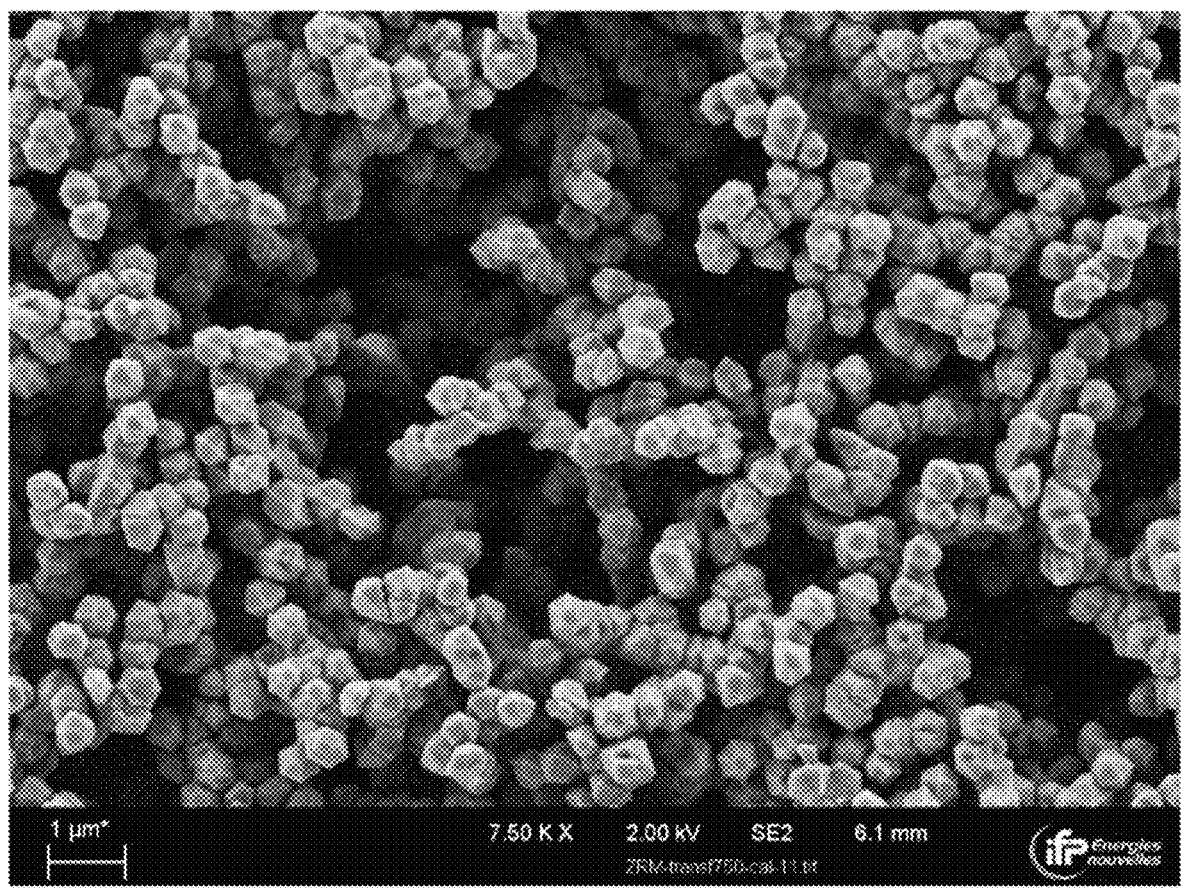
FIG. 3 represents a scanning electron microscope (SEM) image of the AFX zeolite obtained according to Example 7.

The calcined solid product was analyzed by X-ray diffraction and identified as consisting of an AFX-structure zeolite with a purity of greater than 99% by weight. The X-ray diffraction pattern produced for the calcined solid is given in FIG. 2. The image obtained by scanning electron microscopy (SEM) of the calcined AFX-structure solid is given in FIG. 3. The product has an $SiO_2$/$Al_2O_3$ molar ratio of 13.26 as determined by X-ray fluorescence.

Example 8: Preparation of an AFX-Structure Zeolite According to the Invention 542 mg of an FAU-structure zeolite (CBV780, $SiO_2$/$Al_2O_3$=98.22, Zeolyst, LOI=8.52%) were mixed with 2.085 g of an aqueous solution of 1,6-bis(methylpiperidinium) hexane dihydroxide (20.9% by weight) prepared in accordance with Example 1. 3.0 g of deionized water are added to the previous mixture, and the preparation obtained is kept stirring for 10 minutes. 269 mg of an aqueous solution containing 20% by weight of sodium hydroxide (98% by weight, Aldrich) are added to the synthesis mixture and kept stirring for 15 minutes. 56 mg of amorphous aluminum hydroxide gel (amorphous Al(OH)3 gel, 58.55% by mass of Al2O3, Merck), corresponding to an (Al2O3(amorphous gel)/Al2O3 (FAU) molar ratio of 6.68, are then incorporated into the synthesis mixture, which is kept stirring for half an hour to evaporate the solvent until the desired composition of the gel is obtained, i.e. a molar composition of the mixture as follows: 1 SiO2:0.05 Al2O3:0.17 R:0.083 Na2O:34 H2O, i.e. an SiO2/Al2O3 ratio of 20. The mixture is then transferred, after homogenization, into an autoclave. The autoclave is closed and then heated for 6 days at 170° C. with stirring at 35 rpm with a rotary spit system. The crystalline product obtained is filtered off, washed with deionized water and then dried overnight at 100° C. The loss on ignition of the dried solid is 9.5%. The solid is then introduced into a muffle furnace where a calcination step is performed: the calcination cycle comprises an increase in temperature of 1.5° C./minute up to 200° C., a steady stage at 200° C. maintained for 2 hours, an increase in temperature of 1° C./minute up to 550° C., followed by a steady stage at 550° C. maintained for 8 hours, then return to room temperature.

The calcined solid product was analyzed by X-ray diffraction and identified as consisting of an AFX-structure zeolite with a purity of greater than 99% by weight.

Example 9: Preparation of an AFX-Structure Zeolite According to the Invention 3.420 g of an FAU-structure zeolite (CBV780, SiO2/Al2O3=98.22, Zeolyst, LOI=8.52%) were mixed with 13.158 g of an aqueous solution of 1,6-bis(methylpiperidinium)hexane dihydroxide (20.9% by weight) prepared in accordance with Example 1. 18.990 g of deionized water are added to the previous mixture, and the preparation obtained is kept stirring for 10 minutes. 1.697 g of an aqueous solution containing 20% by weight of sodium hydroxide (98% by weight, Aldrich) are added to the synthesis mixture and kept stirring for 15 minutes. 355 mg of amorphous aluminum hydroxide gel (amorphous Al(OH)3 gel, 58.55% by mass of Al2O3, Merck), corresponding to an (Al2O3(amorphous gel)/Al2O3 (FAU) molar ratio of 6.68, are then incorporated into the synthesis mixture, which is kept stirring for half an hour to evaporate the solvent until the desired composition of the precursor gel is obtained, i.e. a molar composition of the mixture as follows: 1 SiO2:0.05 Al2O3:0.17 R:0.083 Na2O:34 H2O, i.e. an SiO2/Al2O3 ratio of 20. The precursor gel is then transferred, after homogenization, into a 160 mL stainless-steel reactor equipped with a stirring system with four inclined paddles. The reactor is closed and then heated for 24 hours at 170° C. with stirring at 250-300 rpm. The crystalline product obtained is filtered off, washed with deionized water and then dried overnight at 100° C. The loss on ignition of the dried solid is 9.7%. The solid is then introduced into a muffle furnace where a calcination step is performed: the calcination cycle comprises an increase in temperature of 1.5° C./minute up to 200° C., a steady stage at 200° C. maintained for 2 hours, an increase in temperature of 1° C./minute up to 550° C., followed by a steady stage at 550° C. maintained for 8 hours, then return to room temperature.

The calcined solid product was analyzed by X-ray diffraction and identified as consisting of an AFX-structure zeolite with a purity of greater than 99% by weight.

The product has an SiO2/Al2O3 molar ratio of 12.6 as determined by X-ray fluorescence.

Example 10: Preparation of an AFX-Structure Zeolite According to the Invention 423 mg of an FAU-structure zeolite (CBV780, SiO2/Al2O3=98.22, Zeolyst, LOI=8.52%) were mixed with 1.626 g of an aqueous solution of 1,6-bis(methylpiperidinium) hexane dihydroxide (20.9% by weight) prepared in accordance with Example 1. 2.347 g of deionized water are added to the previous mixture, and the preparation obtained is kept stirring for 10 minutes. 210 mg of an aqueous solution containing 20% by weight of sodium hydroxide (98% by weight, Aldrich) are added to the synthesis mixture and kept stirring for 15 minutes. 44 mg of amorphous aluminum hydroxide gel (amorphous Al(OH)3 gel, 58.55% by mass of Al2O3, Merck), corresponding to an (Al2O3(amorphous gel)/Al2O3 (FAU) molar ratio of 6.68, are then incorporated into the synthesis mixture, which is kept stirring for half an hour. The molar composition of the precursor gel is as follows: 1 SiO2:0.05 Al2O3:0.17 R:0.08 Na2O:34 H2O, i.e. an SiO2/Al2O3 ratio of 20. The precursor gel is then transferred, after homogenization, into an autoclave. The autoclave is closed and then heated for 40 hours at 170° C. without stirring. The crystalline product obtained is filtered off, washed with deionized water and dried overnight at 100° C. The loss on ignition of the dried solid is 9.7%. The solid is then introduced into a muffle furnace where a calcination step is performed: the calcination cycle comprises an increase in temperature of 1.5° C./minute up to 200° C., a steady stage at 200° C. maintained for 2 hours, an increase in temperature of 1° C./minute up to 550° C., followed by a steady stage at 550° C. maintained for 8 hours, then return to room temperature.

The calcined solid product was analyzed by X-ray diffraction and identified as consisting of an AFX-structure zeolite with a purity of greater than 99% by weight. The product has an SiO2/Al2O3 molar ratio of 18.5 as determined by X-ray fluorescence.

Example 11: Preparation of an AFX-Structure Zeolite According to the Invention 896 mg of an FAU-structure zeolite (CBV780, SiO2/Al2O3=98.22, Zeolyst, LOI=8.52%) were mixed with 4.163 g of an aqueous solution of 1,6-bis(methylpiperidinium) hexane dihydroxide (20.9% by weight) prepared in accordance with Example 1. 7.04 g of deionized water are added to the previous mixture, and the preparation obtained is kept stirring for 10 minutes. 120 mg of sodium hydroxide (98% by weight, Aldrich) were incorporated into the synthesis mixture, which is kept stirring for 15 minutes. 120 mg of amorphous aluminum hydroxide gel (amorphous Al(OH)3 gel, 58.55% by mass of Al2O3, Merck) are then incorporated and the synthesis gel is kept stirring for 15 minutes. Finally, 180 mg of Cab-O-Sil M5 fumed silica (100% by weight of SiO2, Cabot) were incorporated into the synthesis mixture, which is kept stirring for half an hour. The molar composition of the precursor gel is as follows: 1 SiO2:0.05 Al2O3:0.167 R:0.083 Na2O:36.7 H2O, i.e. an SiO2/Al2O3 ratio of 20. The reaction mixture thus contains 74% by mass of anhydrous FAU zeolite relative to the total anhydrous mass of the sources of trivalent and tetravalent elements in the mixture. The precursor gel is then transferred, after homogenization, into an autoclave. The autoclave is closed and then heated for 24 hours at 170° C. with stirring at 35 rpm with a rotary spit system. The crystalline product obtained is filtered off, washed with deionized water and then dried overnight at 100° C. The loss on ignition of the dried solid is 9.9%. The solid is then introduced into a muffle furnace where a calcination step is performed: the calcination cycle comprises an increase in temperature of 1.5° C./minute up to 200° C., a steady stage at 200° C. maintained for 2 hours, an increase in temperature of 1° C./minute up to 550° C., followed by a steady stage at 550° C. maintained for 8 hours, then return to room temperature.

The calcined solid product was analyzed by X-ray diffraction and identified as consisting of an AFX-structure zeolite with a purity of greater than 99% by weight. The product has an SiO2/Al2O3 molar ratio of 14.8 as determined by X-ray fluorescence.

Example 12: Preparation of an AFX-Structure Zeolite According to the Invention 1645 g of an FAU-structure zeolite (CBV780, SiO2/Al2O3=95.97, Zeolyst, LOI=9.30%) were mixed with 6424 g of an aqueous solution of 1,6-bis(methylpiperidinium)hexane dihydroxide (18.36% by weight) prepared in accordance with Example 1. 9114 g of deionized water are added to the previous mixture, and the preparation obtained is kept stirring for 10 minutes. 164 g of sodium hydroxide (98% by weight, Aldrich) were incorporated into the synthesis mixture and kept stirring for 15 minutes. 153.85 g of amorphous aluminum hydroxide gel (amorphous Al(OH)3 gel, 58.55% by mass of Al2O3, Merck), corresponding to an (Al2O3 (amorphous gel)/Al2O3 (FAU) molar ratio of 6.49, are then incorporated and the synthesis gel is kept stirring for 15 minutes. The molar composition of the precursor gel is as follows: 1 SiO2:0.05 Al2O3:0.167 R:0.093 Na2O:36.7 H2O, i.e. an SiO2/Al2O3 ratio of 20. The precursor gel is then transferred, after homogenization, into a 25 L stainless-steel reactor. The reactor is closed and then heated for 23 hours at 170° C. under autogenous pressure and with stirring at 200 rpm using a system with four inclined paddles. The crystalline product obtained is filtered off, washed with deionized water and then dried overnight at 100° C. The loss on ignition of the dried solid is 9.7%. The solid is then introduced into a muffle furnace where a calcination step is performed: the calcination cycle comprises an increase in temperature of 1.5° C./minute up to 200° C., a steady stage at 200° C. maintained for 2 hours, an increase in temperature of 1° C./minute up to 550° C., followed by a steady stage at 550° C. maintained for 8 hours, then return to room temperature.

The calcined solid product was analyzed by X-ray diffraction and identified as consisting of an AFX-structure zeolite with a purity of greater than 99% by weight. The product has an SiO2/Al2O3 molar ratio of 14.8 as determined by X-ray fluorescence.

Example 13: Preparation of an AFX-Structure Zeolite According to the Invention 7.38 g of an FAU-structure zeolite (CBV780, SiO2/Al2O3=98.22, Zeolyst, LOI=8.52%) were mixed with 8.75 g of an aqueous solution of 1,6-bis(methylpiperidinium)hexane dihydroxide (18.36% by weight) prepared in accordance with Example 1. 100 g of mother liquor, i.e. the liquid obtained after the first filtration of the suspension of AFX zeolite obtained after the hydrothermal treatment in Example 12, are added to the previous mixture, and the preparation obtained is kept stirring for 10 minutes. 0.5 g of sodium hydroxide (98% by weight, Aldrich) were incorporated into the synthesis mixture and kept stirring for 15 minutes. 1.026 g of amorphous aluminum hydroxide gel (amorphous Al(OH)3 gel, 58.55% by mass of Al2O3, Merck), corresponding to an (Al2O3(amorphous gel)/Al2O3 (FAU) molar ratio of 6.49, are then incorporated and the synthesis gel is kept stirring for 15 minutes. The molar composition of the precursor gel is as follows: 1 SiO2:0.05 Al2O3:0.167 R:0.093 Na2O:36.7 H2O, i.e. an SiO2/Al2O3 ratio of 20. The precursor gel is then transferred, after homogenization, into a 160 mL stainless-steel reactor. The reactor is closed and then heated for 23 hours at 170° C. under autogenous pressure and with stirring at 200 rpm using a system with four inclined paddles. The crystalline product obtained is filtered off, washed with deionized water and then dried overnight at 100° C. The loss on ignition of the dried solid is 10.1%. The solid is then introduced into a muffle furnace where a calcination step is performed: the calcination cycle comprises an increase in temperature of 1.5° C./minute up to 200° C., a steady stage at 200° C. maintained for 2 hours, an increase in temperature of 1° C./minute up to 550° C., followed by a steady stage at 550° C. maintained for 8 hours, then return to room temperature.

The calcined solid product was analyzed by X-ray diffraction and identified as consisting of an AFX-structure zeolite with a purity of greater than 99% by weight. The product has an SiO2/Al2O3 molar ratio of 14 as determined by X-ray fluorescence.

The invention claimed is:

1. A process for preparing an AFX-structure zeolite comprising at least the following steps:
   i) mixing, in an aqueous medium, an FAU-structure zeolite having an $SiO_{2\ (FAU)}/Al_2O_{3\ (FAU)}$ molar ratio of between 6.00 and 200, an organic nitrogenous compound R, R being chosen from 1,5-bis(methylpiperidinium)pentane dihydroxide,
   1,6-bis(methylpiperidinium)hexane dihydroxide or
   1,7-bis(methylpiperidinium)heptane dihydroxide, at least one source of at least one alkali and/or alkaline-earth metal M of valency n, n being an integer greater than or equal to 1, M being chosen from lithium, potassium, sodium, magnesium and calcium and a mixture of at least two of these metals, the reaction mixture having the following molar composition:

$(SiO_{2\ (FAU)})/(Al_2O_{3\ (FAU)})$ between 6.00 and 200,
   $H_2O/(SiO_{2\ (FAU)})$ between 1.00 and 100,
   $R/(SiO_{2\ (FAU)})$ between 0.01 and 0.60,
   $M_{2/n}O/(SiO_{2\ (FAU)})$ between 0.005 and 0.45, in which $SiO_{2\ (FAU)}$ denotes the amount of $SiO_2$ provided by the FAU zeolite and $Al_2O_{3\ (FAU)}$ denotes the amount of $Al_2O_3$ provided by the FAU zeolite, until a homogeneous precursor gel is obtained;
   ii) hydrothermal treatment of said precursor gel obtained on conclusion of step i) at a temperature of between 120° C. and 220° C., for a time of between 12 hours and 15 days.

2. The process as claimed in claim 1, in which R is 1,6-bis(methylpiperidinium)hexane dihydroxide.

3. The process as claimed in claim 1, in which M is sodium.

4. The process as claimed in claim 3, in which the source of at least one alkali and/or alkaline-earth metal M is sodium hydroxide.

5. The process as claimed in claim 1, in which the reaction mixture of step i) includes at least one additional source of an $XO_2$ oxide, X being one or more tetravalent element(s) chosen from the group formed by the following elements: silicon, germanium, titanium, such that the $XO_2/SiO_{2\ (FAU)}$ molar ratio is between 0.001 and 1, the $SiO_{2\,(FAU)}$ content in said ratio being the content provided by the FAU-structure zeolite.

6. The process as claimed in claim 5, in which the reaction mixture of step i) has the following molar composition:
$(XO_2+SiO_{2\,(FAU)})/Al_2O_{3\,(FAU)}$ between 6.00 and 200,
$H_2O/(XO_2+SiO_{2\,(FAU)})$ between 1 and 100,
$R/(XO_2+SiO_{2\,(FAU)})$ between 0.01 and 0.6,
$M_{2/n}O/(XO_2+SiO_{2\,(FAU)})$ between 0.005 and 0.45.

7. The process as claimed in claim 5, in which X is silicon.

8. The process as claimed in claim 1, in which the reaction mixture of step i) includes at least one additional source of a $Y_2O_3$ oxide, Y being one or more trivalent element(s) chosen from the group formed by the following elements: aluminum, boron, gallium, such that the $Y_2O_3/Al_2O_{3\,(FAU)}$ molar ratio is between 0.001 and 10, the $Al_2O_{3\,(FAU)}$ content in said ratio being the content provided by the FAU-structure zeolite.

9. The process as claimed in claim 8, in which the reaction mixture of step i) has the following molar composition:
$SiO_{2\,(FAU)}/(Al_2O_{3\,(FAU)}+Y_2O_3)$ between 6.00 and 200,
$H_2O/SiO_{2\,(FAU)}$ between 1 and 100,
$R/SiO_{2\,(FAU)}$ between 0.01 and 0.6,
$M_{2/n}O/SiO_{2\,(FAU)}$ between 0.005 and 0.45,
$SiO_{2\,(FAU)}$ being the amount of $SiO_2$ provided by the FAU zeolite and $Al_2O_{3\,(FAU)}$ being the amount of $Al_2O_3$ provided by the FAU zeolite.

10. The process as claimed in claim 8, in which Y is aluminum.

11. The process as claimed in claim 1, in which the reaction mixture of step i) contains:
at least one additional source of an $XO_2$ oxide
and at least one additional source of a $Y_2O_3$ oxide,
the FAU zeolite representing between 5 and 95% by mass relative to the total amount of trivalent and tetravalent elements $SiO_{2\,(FAU)}$, $XO_2$, $Al_2O_{3\,(FAU)}$ and $Y_2O_3$ in the reaction mixture, and the reaction mixture having the following molar composition:
$(XO_2+SiO_{2\,(FAU)})/(Al_2O_{3\,(FAU)}+Y_2O_3)$ between 6.00 and 200,
$H_2O/(XO_2+SiO_{2\,(FAU)})$ between 1 and 100,
$R/(XO_2+SiO_{2\,(FAU)})$ between 0.01 and 0.6,
$M_{2/n}O/(XO_2+SiO_{2\,(FAU)})$ between 0.005 and 0.45.

12. The process as claimed in claim 1, in which the precursor gel obtained on conclusion of step i) has a molar ratio of the total amount expressed as oxides of tetravalent elements to the total amount expressed as oxides of trivalent elements of between 6.00 and 100.

13. The process as claimed in claim 1, in which the FAU-structure zeolite has an $SiO_2/Al_2O_3$ molar ratio of between 6.00 and 100.

14. The process as claimed in claim 1, in which seed crystals of an AFX-structure zeolite are added to the reaction mixture of step i), said seed crystals not being taken into account in the total mass of the sources of the tetravalent and trivalent elements.

15. The process as claimed in claim 1, in which step i) comprises a step of maturing the reaction mixture at a temperature of between 20 and 100° C., with or without stirring, for a time of between 30 minutes and 48 hours.

16. The process as claimed in claim 1, in which the hydrothermal treatment of step ii) is performed under autogenous pressure at a temperature of between 120° C. and 220° C. for a time of between 12 hours and 12 days.

17. The process as claimed in claim 1, in which the solid phase obtained on conclusion of step ii) is filtered off, washed, and dried at a temperature of between 20 and 150° C. for a time of between 5 and 24 hours, to obtain a dried zeolite.

18. The process as claimed in claim 17, in which the dried zeolite is then calcined at a temperature of between 450 and 700° C. for a time of between 2 and 20 hours, the calcination possibly being preceded by a gradual temperature increase.

19. The process as claimed in claim 1, in which the reaction mixture has the following molar composition:
(SiO2 (FAU))/(Al2O3 (FAU)) between 6.00 and 100,
H2O/(SiO2 (FAU)) between 5 and 60,
R/(SiO2 (FAU)) between 0.05 and 0.50, and
M2/nO/(SiO2 (FAU)) between 0.05 and 0.25.

20. An AFX-structure zeolite having an $SiO_2/Al_2O_3$ ratio of between 4.00 and 100 and having an AFX structure phase purity greater than 99% by weight, the AFX-structure zeolite being obtained.

* * * * *